(12) United States Patent
Voic

(10) Patent No.: US 9,387,005 B2
(45) Date of Patent: Jul. 12, 2016

(54) ULTRASONIC CUTTING BLADE WITH COOLING LIQUID CONDUCTION

(71) Applicant: Misonix Incorporated, Farmingdale, NY (US)

(72) Inventor: Dan Voic, Cedar Grove, NJ (US)

(73) Assignee: MISONIX, INCORPORATED, Farmingdale, NY (US)

( * ) Notice: Subject to any disclaimer, the term of this patent is extended or adjusted under 35 U.S.C. 154(b) by 288 days.

(21) Appl. No.: 13/931,003

(22) Filed: Jun. 28, 2013

(65) Prior Publication Data

US 2015/0005771 A1    Jan. 1, 2015

(51) Int. Cl.
*A61B 17/32* (2006.01)
*A61B 17/16* (2006.01)
*A61B 17/14* (2006.01)

(52) U.S. Cl.
CPC ......... *A61B 17/320068* (2013.01); *A61B 17/14* (2013.01); *A61B 2017/320072* (2013.01); *A61B 2217/007* (2013.01)

(58) Field of Classification Search
CPC .............................................. A61B 17/320068
USPC ................................................. D24/144, 146
See application file for complete search history.

(56) References Cited

U.S. PATENT DOCUMENTS

| | | | | |
|---|---|---|---|---|
| 4,963,153 | A * | 10/1990 | Noesberger | A61F 2/389 623/20.3 |
| 5,167,725 | A * | 12/1992 | Clark | A61B 17/320068 148/427 |
| 5,205,817 | A * | 4/1993 | Idemoto | A61B 17/320068 604/22 |
| 5,261,922 | A * | 11/1993 | Hood | A61B 17/320068 30/355 |
| 6,283,981 | B1 * | 9/2001 | Beaupre | A61B 17/320068 606/169 |
| 6,379,371 | B1 * | 4/2002 | Novak | A61B 17/320068 30/123.3 |
| 6,443,969 | B1 * | 9/2002 | Novak | A61B 17/320068 606/169 |
| 8,343,178 | B2 * | 1/2013 | Novak | A61B 17/320068 606/169 |
| D680,218 | S * | 4/2013 | Darian | D24/144 |
| 2002/0077550 | A1 * | 6/2002 | Rabiner | A61B 17/22012 600/439 |
| 2003/0204199 | A1 * | 10/2003 | Novak | A61B 17/320068 606/169 |
| 2004/0030254 | A1 * | 2/2004 | Babaev | A61B 17/320068 600/459 |
| 2005/0177184 | A1 * | 8/2005 | Easley | A61B 17/1659 606/167 |
| 2007/0233131 | A1 * | 10/2007 | Song | A61B 17/1671 606/79 |
| 2008/0058775 | A1 * | 3/2008 | Darian | A61B 17/320068 606/1 |
| 2008/0183109 | A1 * | 7/2008 | Babaev | A61B 17/320068 601/2 |
| 2011/0105958 | A1 * | 5/2011 | Babaev | A61N 7/022 601/2 |
| 2011/0160624 | A1 * | 6/2011 | Babaev | A61B 17/320068 601/2 |
| 2015/0088179 | A1 * | 3/2015 | Voic | A61B 17/320068 606/169 |

FOREIGN PATENT DOCUMENTS

SU    1424813 A1    9/1988

* cited by examiner

*Primary Examiner* — Christian Sevilla
(74) *Attorney, Agent, or Firm* — R. Neil Sudol; Henry D. Coleman

(57) ABSTRACT

An ultrasonic surgical tool comprises a substantially planar blade body having a pair of opposed lateral surfaces and a cutting edge. A shank integral on a distal side with the blade body is provided at a proximal side with a connector for operatively linking the blade to a source of ultrasonic mechanical vibrations. The blade body is provided in at least one of the lateral surfaces with a shallow recess which is nearly coextensive with that lateral surface. The blade body has a raised rim surrounding and defining the recess, the rim being narrow on the three sides between the recess and the cutting edge.

4 Claims, 3 Drawing Sheets

ULTRASONIC CUTTING BLADE WITH COOLING LIQUID CONDUCTION

FIELD OF THE INVENTION

This invention relates to an ultrasonic tool. More particularly, this invention relates to an ultrasonic cutting blade. The blade is particularly useful in a surgical application to cut tissue such as cartilage and bone. The present invention is also directed in part to an associated surgical method.

BACKGROUND OF THE INVENTION

In the field of orthopedics, the cutting of living bone is a prerequisite for many procedures. Such procedures include the reconstruction of damaged tissue structures due to accidents, the grafting of healthy bone into areas damaged by disease, or the correction of congenital facial abnormalities like a receding chin line. Over several centuries, these tasks were performed through the utilization of devices called bone saws.

Traditional bone saws are categorized into several basic categories. Hand powered saws or drills are just that, hand held devices which require the operator to move the device in a fashion similar to that used for carpentry tools. Powered devices, whether electric or pneumatic, are of either the reciprocating or rotary type. The reciprocating devices use a flat, sword like blade where the back and forth motion is provided by a motor instead of the hand. The rotary devices use a rotating motor to spin a drill bit or a blade that has teeth arranged around its circumference similar to a table saw blade. All of these traditional bone saws are used today in medical procedures around the world.

While traditional saws are functional, they have many disadvantages. With either the band or reciprocating saws, for instance, it is not easy to initiate and direct a cut. A cut must start from an edge or, alternatively, a starting hole must be used. To create a starting hole, a drill or similar instrument is operated to bore into the bone. Subsequently, a cutting blade is inserted into the bored hole. The user can then proceed to cut. Alternatively, a rotary type blade may be used. However, when a rotary blade is used, the cut must follow a relatively straight path to prevent the blade from binding in the cut. With all blades the ability to create a curved or compound angle cut is extremely limited by the blade chosen. The relatively thick blades have a wide kerf, so that a significant thickness of the viable bone is lost in the cutting procedure. Physicians would like this width to be as thin as possible in most procedures where reconstruction is necessary.

Above all, the relatively slow linear or tangential speeds of conventional bone saw blades coupled with the teeth necessary for cutting result in high frictional losses, which becomes manifested as heat. Heat will cause necrosis of the tissue if the bone temperatures reach 47° C. for more than a few seconds. When tissue necroses, the bone recedes after the surgery as the necrotic bone is overgrown. During such natural postsurgical tissue developments, the thickness of the cuts in the bone actually increases. The bone rescission process must be complete before healing can begin. To prevent the shortening of the length of the bone, metal plates and screws are used to fix the bone fragments in proper position. All of these factors obviously lead to increased operative time, and more importantly, to dramatically increased healing time, since the bone must knit across a greater span. Some studies have shown the strength of the bone to be effected negatively as well When an upper or lower jaw is to be cut in elective surgery, the heating effect of traditional saws requires even more extraordinary intervention to prevent damage. Cutting the jaw between the teeth will cause loss of teeth if the bone is damaged or does not heal quickly. To prevent the tooth loss, the teeth must be spread apart preoperatively; sometimes forcing the patient to wear braces for up to 6 months before the operation can take place. In these cases, the costs and patient discomfort increases dramatically.

To limit the tissue temperature rise in an attempt to reduce necrosis, some traditional surgical saws provide cooling liquid to the surgical site. See, for instance, U.S. Pat. No. 4,008,720 to Brinckmann et al. These devices typically introduce coolant into spaces between segments on the cutting edge or rely on spray methods to flood the cutting site with fluid. Another technique employed by clinicians is to make very light cuts and increase the time between passes of the tool. Coupled with irrigation of the area, bone temperature rise is reduced measurably. Of course, this technique increases operative time and clinician fatigue.

Several researchers have proposed the use of ultrasonic tools for bone separation. The use of ultrasonic surgical instruments for cutting through various tissues is well known. While these devices are superior to the traditional saws in several aspects such as reduced kerf size, reduced noise, and superior ability for making complex geometric cuts, the temperature rise in bone due to frictional heating at the blade/tissue interface is still a significant problem. The problem is exacerbated with the use of ultrasonics due to the rapid motion involved as compared to that of traditional reciprocating saws. Some designers have tried to reduce heating by modifying the cross-section of the cutting blade. U.S. Pat. No. 5,188,102 to Idernoto, U.S. Pat. No. 4,188,952 to Loschilov, and U.S. Pat. No. 5,261,922 to Hood all show designs for cutting which have modified cross sections to reduce frictional heating.

Several ultrasonic devices have provided cooling to the cutting blade with varied degrees of success. U.S. Pat. No. 4,823,790 to Alperovich et al. shows a design for a cryogenically cooled scalpel blade. However, this design may actually damage viable tissue by freezing. In addition, this design does not provide any coolant to surrounding tissue not in direct contact with the blade.

U.S. Pat. Nos. 5,205,817, 5,188,102, and 4,832,683 all to Idemoto show examples of ultrasonic instruments with provisions for fluid cooling. These instruments, however, either do not provide optimal coolant flow where it is needed, mainly at the cutting portion of the blade, or for ones that do provide coolant at the tip, they interrupt the cutting edge with holes for the coolant. An interrupted, uneven cutting edge hinders manipulation and makes it difficult to guide the blade on the bone surface.

One phenomenon associated with ultrasonic tooling which acts to hinder the beneficial effects of irrigating the operative site is ultrasonic atomization. When an ultrasonically vibrating body is brought into contact with fluid, that fluid is broken into small droplets, which have a size inversely proportional to the frequency of vibration. In other words, the higher the frequency, the smaller and more mobile the liquid drop. Droplets created by ultrasonic vibrations can be very small in size, with some being less than 1 micron in diameter. This phenomenon is well known to the art. In fact, many devices intended to atomize liquid, such as room humidifiers, medical nebulizers, and industrial spray nozzle are based upon this principle. In the operating theater, however, the presence of nebulized particles is not appreciated, since these particles may contain viral or bacterial agents. Also, some of the fluid will be atomized before reaching the operative site, reducing the cooling efficiency. An effective way to insure the liquid transport is needed.

U.S. Pat. No. 6,379,371 discloses an ultrasonic surgical blade with cooling, which has a blade body with a smooth continuous cutting edge and a shank connected at one end to the blade body and operatively connectable at an opposite end to a source of ultrasonic vibrations. The shank is provided with an axially extending bore for the conveyance of cooling fluid to the cutting edge, while the blade body is provided with an axially extending through-slot communicating at one end with the bore. The blade body is preferably provided at an end opposite the shank with a recess communicating, with the bore for distributing fluid from the slot towards the cutting edge. The recess may have a configuration that parallels at least a portion of the cutting edge. Where the cutting edge is circular and the blade body has a planar surface between the fluid distribution guide surface and the cutting edge, for instance, the recess has a fluid distribution surface inclined with respect to the planar blade surface and extending along a circular arc.

SUMMARY OF THE INVENTION

The present invention aims to provide an improved ultrasonic tool or probe which has an improved cooling capability. An ultrasonic tool or probe in accordance with the invention may particularly take the form of ultrasonic cutting blade which allows thin kerf cuts, does not require predrilled holes for cutting, allows complex geometric cuts, has a continuous cutting surface, and provides for liquid irrigation at primarily the blade/tissue interface. More specifically, the present invention pertains to an ultrasonically vibrated cutting blade with an improved provision for delivery of a cooling medium for reducing and limiting thermal damage to living tissue. The present invention specifically targets the application of cutting viable bones in surgery, although the device is not exclusive to this application.

An ultrasonic surgical tool comprises, in accordance with the present invention, a substantially planar blade body having a pair of opposed lateral surfaces and a cutting edge. A shank integral on a distal side with the blade body is provided at a proximal side with a connector for operatively linking the blade to a source of ultrasonic mechanical vibrations. The blade body is provided in at least one of the lateral surfaces with a shallow recess, which is nearly coextensive with the respective lateral surface. The blade body has a raised rim surrounding and defining the recess, the rim being narrow on the three sides. On the fourth, proximal, side of the recess, a proximal portion of the blade body, which merges with the shank, bounds the recess.

The blade body is preferably provided with a through hole in the recess. The through hole extends between the lateral surfaces of the blade body and enables liquid flow from the recess to an opposing side of the blade body.

The shank is preferably provided with a bore or channel having an outlet communicating with the recess, thereby enabling liquid flow into the recess from a source connected to the channel.

The through hole may extend in a proximal direction to a proximal end of the recess or recesses. In that case the through hole is continuous with the bore or channel at the outlet thereof.

In a preferred embodiment of the present invention, the recess is one of two recesses each provided in a respective one of the lateral blade surfaces, each recess being defined by a surrounding rim. The through hole enables liquid communication between the recesses.

Each of the recesses occupies a major portion of the respective lateral surface. Each recess is defined in substantial part by a shallow wall formed by the rim on three ides and the proximal portion of the blade body on the proximal side. Where the shank is provided with a liquid-delivery bore or channel, the bore or channel may communicate with each recess, either via separate outlet holes or via a single outlet opening onto both lateral blade surfaces.

Pursuant to another feature of the present invention, the blade body and the recess are elongate and the through hole is an elongate narrow opening, i.e., a slot.

An ultrasonic surgical tool comprises, in accordance with the present invention, a substantially planar blade body having a pair of opposed major faces and a peripheral flange extending along three sides of the blade body. The flange defines a recess in at least one of the opposed major faces. The recess is substantially coextensive with the blade body, that is, occupies nearly all of the respective major face of the blade body. At least a portion of the flange has a cutting edge or surface. A shank integral on a distal side with the blade body is provided at a proximal side with a connector for operatively linking the blade to a source of ultrasonic mechanical vibration.

Other features of the present invention are described above, namely, the provision of two recesses each on a respective major surface of the blade body, the slot in the blade body, the liquid delivery bore or channel and the arrangement of liquid outlets in the recess or recesses. Where there are two recesses on opposing sides of the blade body, each of the recesses is defined on three sides by the flange. In that case, the flange projects in opposite directions from the place of the blade body orthogonally thereto. The proximal end of the blade body has a thickness equal to that of the flange and defined the recess or recesses on a proximal side thereof.

DETAILED DESCRIPTION

Figure 1:
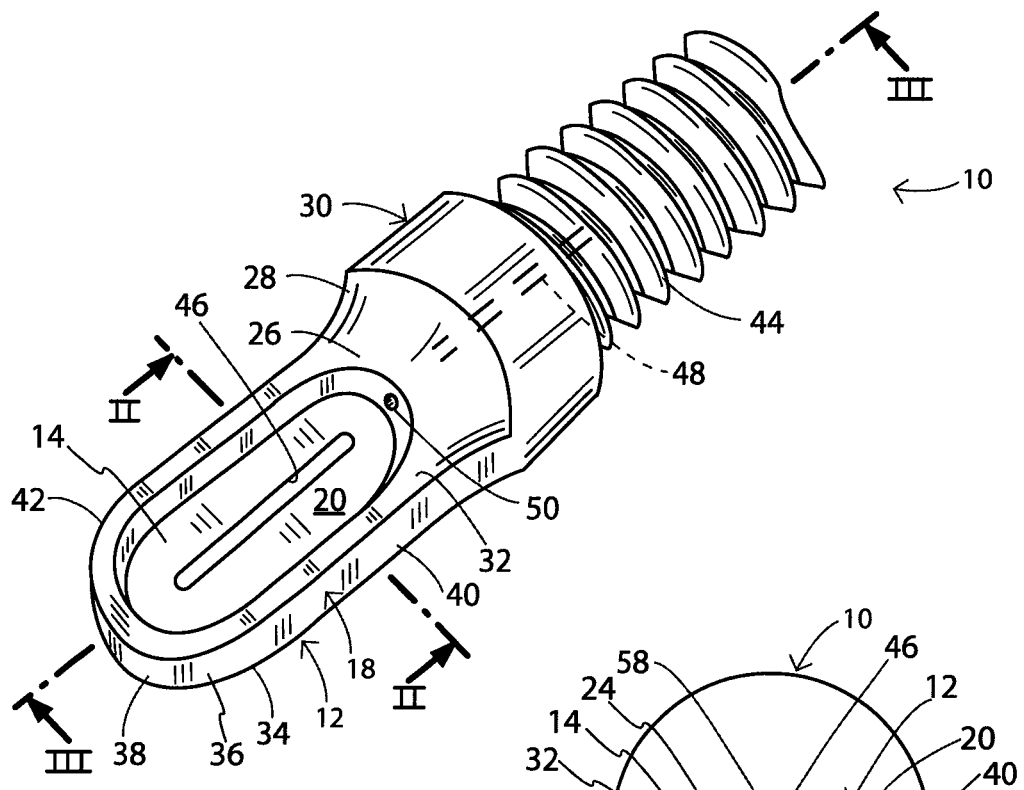
FIG. 1 is a schematic isometric view of an ultrasonic surgical tool in accordance with the present invention.
Figure 2:
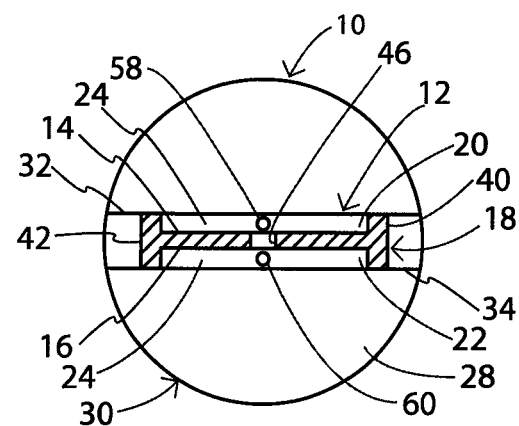
FIG. 2 is a schematic cross-sectional view taken along line II-II in FIG. 1, showing a modified design of the ultrasonic surgical tool on a smaller scale.
Figure 3:
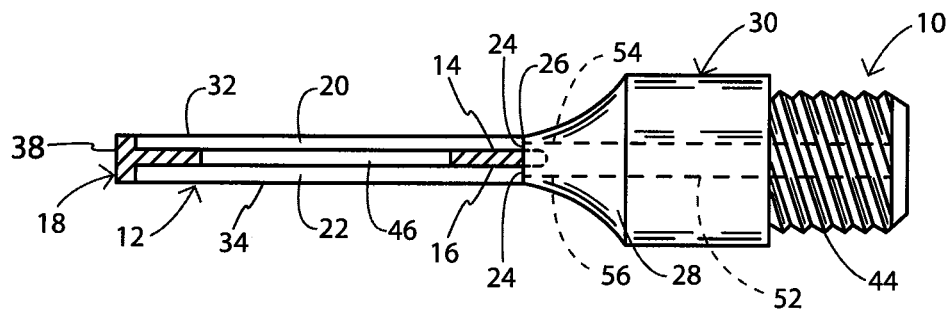
FIG. 3 is a schematic partially cross-sectional view taken along line II-II in FIG. 1 and shows the modified design of FIG. 2.

As depicted in FIGS. 1-3, an ultrasonic surgical tool 10 comprises a substantially planar blade body 12 having a pair of opposed major sides (not separately enumerated) provided with recessed surfaces 14 and 16 and a flange 18 extending around the recessed surfaces 14 and 16 on three sides thereof to define therewith a pair of opposing shallow recesses 20 and 22. Flange 18 extends away from recessed surfaces 14 and 16, generally orthogonally or perpendicularly to the planes (not separately designated) of those surfaces. Flange 18 serves as a rim or sidewall for each recess 20 and 22. Recesses 20 and 22 are delimited on a proximal side of blade body 12 by respective sidewalls 24 continuous with flange 18 and formed by a proximal blade body portion 26 that merges with a tapered portion 28 of a blade shank 30.

Blade body 12 accordingly has a pair of opposed lateral surfaces 32 and 34 that are planar outer surfaces of proximal blade body portion 26 and flange 18. Recessed surfaces 14 and 16 are parallel to and inwardly spaced from lateral surfaces 32 and 34.

Recesses 20 and 22 occupy nearly the entirety of blade body 12 along the opposite major sides thereof. Flange or rim 18 is a narrow strip surrounding the recesses 20 and 22. An outwardly facing surface 36 of flange 18 includes a cutting edge or surface, at least at a distal tip 38 of blade body 12 and optionally along one or both lateral sides 40 and 42 of blade body 12.

Shank 30 is integral on a distal side with blade body 12 and is provided at a proximal side with an externally threaded connector 44 for operatively linking the blade to a source (not shown) of ultrasonic mechanical vibrations. Typically, connector 44 screws into a receptacle on a handpiece, the handpiece housing a piezoelectric crystal stack that generates ultrasonic vibrational energy in response to an electrical waveform input of an ultrasonic frequency.

Blade body 12 is provided with a through hole 46 extending between recessed surfaces 14 and 16 and providing a path of fluid communication between recesses 20 and 22.

Shank 28 is provided with a bore or channel 48 having, in one embodiment of the ultrasonic surgical tool 10, a single outlet port 50 communicating directly with one recess 20. Bore or channel 48 is connectable to a source of irrigant or cooling liquid and guides the liquid into recess 20 via outlet port 50. The irrigant or cooling liquid enters the other recess 22 via through hole 46. Outlet port 50 is disposed at a proximal end of recess 20, in sidewall 24, and at a distance from through hole 46.

As shown in FIGS. 2 and 3, bore or channel 48 may include a central axial upstream section 52 and a pair of branching downstream sections 54 and 56 terminating in respective outlet ports 58 and 60. Outlet ports 58 and 60 are located in proximal sidewalls 24 of recesses 20 and 22. Recesses 20 and 22 therefore each receive irrigant or cooling liquid from bore or channel 48 via respective outlets 58 and 60. Through hole 48 may be eliminated but is preferably retained for pressure equalization and the resulting enhanced fluid flow.

Figure 4:
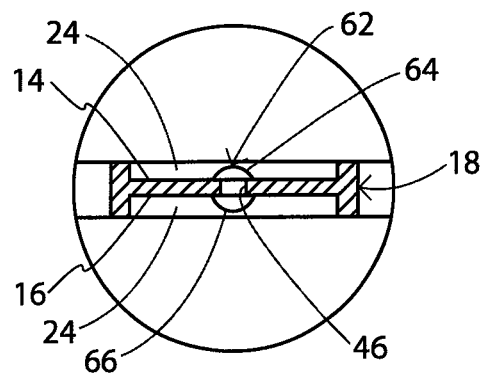
FIG. 4 is a schematic cross-sectional view similar to FIG. 2, showing another modified design on a reduced scale.
Figure 5:
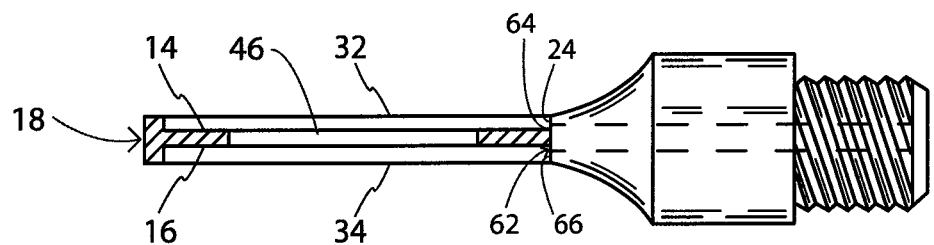
FIG. 5 is a schematic partial cross-sectional view similar to FIG. 3, showing the modified design of FIG. 4.

As depicted in FIGS. 4 and 5, bore or channel 48 may extend distally to an outlet opening 62 in sidewalls 24 of recesses 20 and 22. Recessed surfaces 14 and 16 define a web or septum (not separately designated) that bifurcates outlet opening 62 to form a pair of D-shaped output ports 64 and 66.

Recesses 20 and 22 allow for improved irrigant delivery at a blade tissue interface, both along lateral surfaces 32 and 34 and cutting edge 38, as well as along lateral surfaces 68 and 70 of flange or sidewall rim 18. Lateral surfaces 68 and 70 may serve as additional cutting edges of blade body 12.

Figure 6:
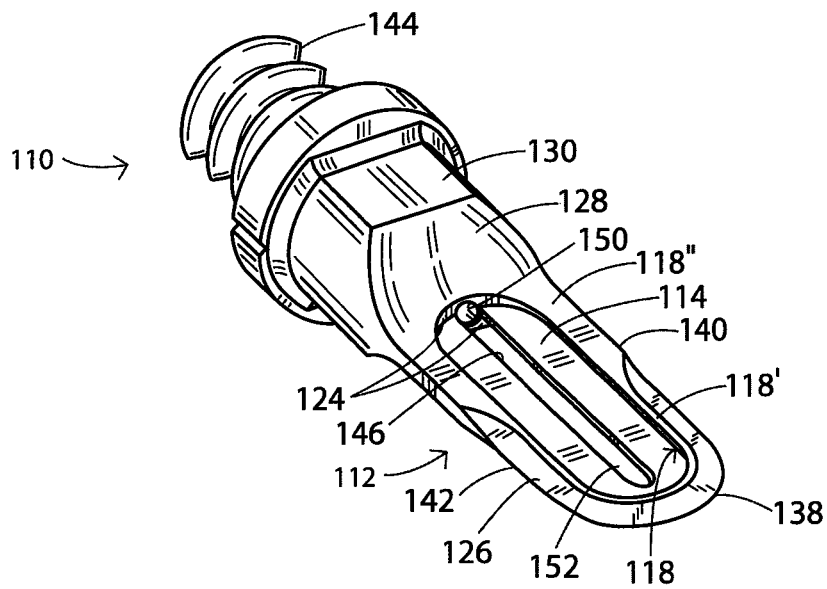
FIG. 6 is an isometric view of another ultrasonic surgical tool in accordance with the present invention.
Figure 7:
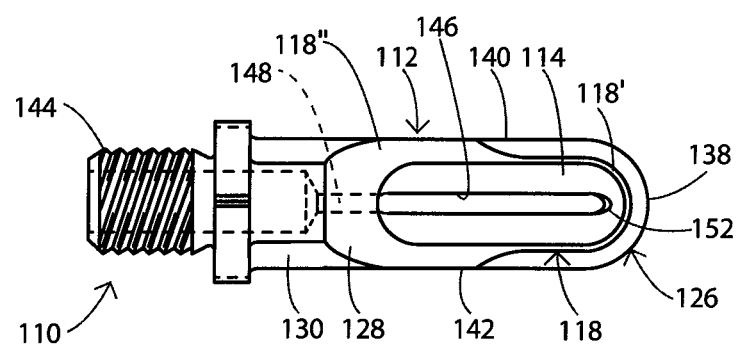
FIG. 7 is a top plan view of the ultrasonic surgical tool of FIG. 6.
Figure 8:
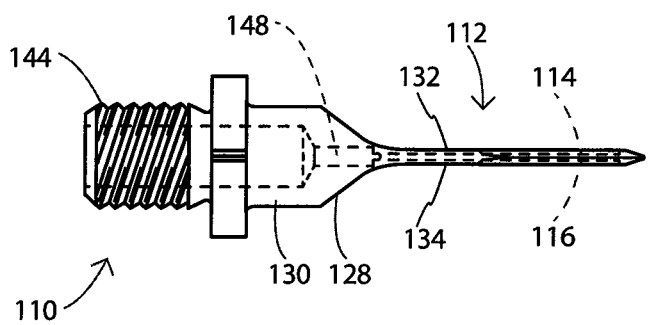
FIG. 8 is a side elevational view of the ultrasonic surgical tool of FIGS. 6 and 7.'

As depicted in FIGS. 6-8, an ultrasonic surgical tool 110 comprises a substantially planar blade body 112 having a pair of opposed major sides (not separately enumerated) provided with recessed surfaces 114 and 116 and a flange or shoulder 118 extending around the recessed surfaces 114 and 116 on three sides thereof to define therewith a pair of opposing shallow recesses (not separately designated). Flange 118 is staggered away from recessed surfaces 114 and 116, generally orthogonally or perpendicularly to the planes of those surfaces. Flange 118 serves as a rim or sidewall that together with recessed surfaces 114 and 116 defined the recesses. The recesses are delimited on a proximal side of blade body 12 by respective sidewalls 124 continuous with flange 118 and formed by a tapered portion 128 of a blade shank 130.

Blade body 112 accordingly has a pair of opposed lateral surfaces 132 and 134 (FIG. 8) that are planar outer surfaces of flange 118 and that are continuous with respective sloped outer surfaces (not designated) of tapered shank portion 128. Recessed surfaces 114 and 116 are parallel to and inwardly spaced from lateral surfaces 132 and 134.

Recessed surfaces 114 and 116 and accordingly the associated recesses occupy nearly the entirety of blade body 112 along the opposite major sides thereof, excepting a beveled cutting edge 126 that arcs about a distal tip 138 of blade body 112 and partially along a distal end of lateral sides 140 and 142 of blade body 112. Along a distal end segment of blade body 112, flange or rim 118 is a narrow strip 118' sandwiched between the recessed surfaces 114 and 116 and beveled cutting edge 126. On a proximal side of the blade body 112, flange or rim 118 is a broader strip 118" extending along the lateral sides 140 and 142 of blade body 112

Shank 130 is integral on a distal side with blade body 112 and is provided at a proximal side with an externally threaded connector 144 for operatively linking the blade to a source (not shown) of ultrasonic mechanical vibrations. Typically, connector 144 screws into a receptacle on a handpiece, the handpiece housing a piezoelectric crystal stack that generates ultrasonic vibrational energy in response to an electrical waveform input of an ultrasonic frequency.

Blade body 112 is provided with an elongate through hole or slot 146 extending between recessed surfaces 114 and 116 and providing a path of fluid communication between the recesses on opposing major sides of blade body 112.

Shank 128 is provided with a bore or channel 148 having a single outlet port 150 communicating directly with elongate through hole or slot 146 as well as the opposed recesses on the opposing major sides of blade body 112. Through hole or slot 146 extends in the proximal direction all the way to sidewalls 124 and is continuous with bore or channel 148 at outlet port 150. Bore or channel 148 is connectable to a source of irrigant or cooling liquid and guides the liquid into through hole or slot 146 and the opposed shallow recesses via outlet port 150.

Recessed surfaces 114 and 116 allow for improved irrigant delivery at a blade tissue interface, both along lateral surfaces 132 and 134 and cutting edge 126. Blade body 112 may be formed at a distal end of slot 146 with a beveled or sloped extension 152 facilitating irrigant movement from slot 146 towards the portion of cutting edge 126 at distal tip 138, so that the irrigant is distributed along the distal tip.

Although the invention has been described in terms of particular embodiments and applications, one of ordinary skill in the art, in light of this teaching, can generate additional embodiments and modifications without departing from the spirit of or exceeding the scope of the claimed invention. For instance, beveled cutting edge 126 may be provided in the embodiment of FIGS. 1-3 and extend nearly along the entire sides 40 and 42. Accordingly, it is to be understood that the drawings and descriptions herein are proffered by way of example to facilitate comprehension of the invention and should not be construed to limit the scope thereof.

What is claimed is:

1. An ultrasonic surgical tool comprising:

a substantially planar blade body having a pair of opposed lateral surfaces; and a shank integral on a distal side with said blade body and provided at a proximal side with a connector for operatively linking the blade to a source of ultrasonic mechanical vibrations, said blade body being provided in at least one of said lateral surfaces with a shallow recess nearly coextensive with said one of said lateral surfaces, said at least one of said lateral surfaces forming a raised rim surrounding and defining said recess, said rim being narrow on a distal side of said blade body and along two lateral sides of said blade body, said blade body being provided in said recess with a through hole enabling liquid flow from said recess to an opposing side of said blade body, said shank being provided with a bore or channel having an outlet communicating with said recess and enabling liquid flow into said recess from a source connected to said channel, said outlet being disposed at a proximal end of said recess and at a distance from said through hole.

2. The surgical tool of claim 1 wherein said recess is one of two recesses each provided in one of said lateral surfaces, each defined by a surrounding rim, said through hole enabling liquid communication between said recesses.

3. The surgical tool of claim 2 wherein each of said recesses occupies a major portion of a respective major side of said blade body, the rim of each of said recesses defining a shallow sidewall extending parallel to said distal side and said lateral sides of said blade body.

4. The surgical tool of claim 1 wherein said blade body and said recess are elongate and said through hole is a slot.

\* \* \* \* \*